Figure 1:
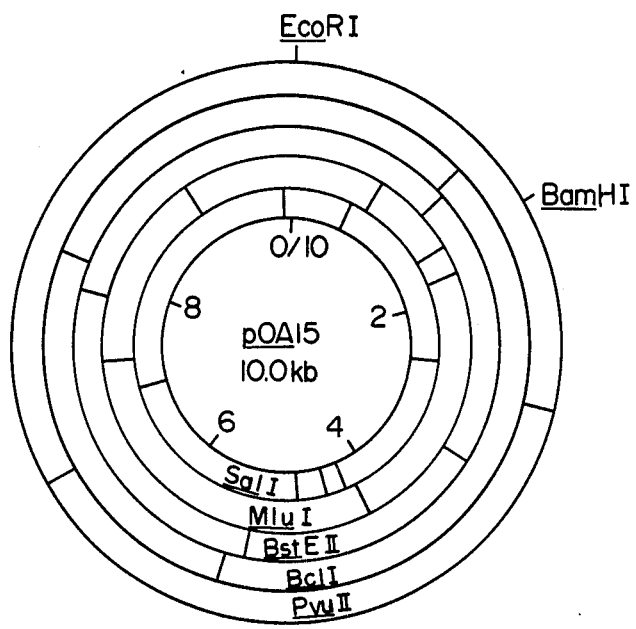

United States Patent [19]

Aiba et al.

[11] Patent Number: 4,615,980
[45] Date of Patent: Oct. 7, 1986

[54] PLASMID POA15

[75] Inventors: Shuichi Aiba, Suita; Tetsuo Ohnuki, Minoo, both of Japan

[73] Assignee: Sanraku-Ocean Co., Ltd., Tokyo, Japan

[21] Appl. No.: 575,848

[22] Filed: Feb. 1, 1984

[30] Foreign Application Priority Data

Feb. 3, 1983 [JP] Japan .................................. 58-15515

[51] Int. Cl.⁴ .......................... C12N 1/00; C12N 15/00
[52] U.S. Cl. .................................. 435/317; 435/172.3; 935/29; 935/75
[58] Field of Search ....................... 435/172.3, 68, 317; 935/22, 66

[56] References Cited

PUBLICATIONS

Ohnuki et al 1983 "Isolation and Characterization of Pock-Forming Plasmids for *Streptomyces griseus* from Soil Actinomycetes" *Gene* v25 155–59.

*Primary Examiner*—Thomas G. Wiseman
*Assistant Examiner*—Joanne M. Giesser
*Attorney, Agent, or Firm*—Wenderoth, Lind & Ponack

[57] ABSTRACT

A plasmid pOA15 in isolated form having the property of conferring pock-forming ability on *Streptomyces griseus* (ATCC 10137) and a molecular length of about 10 kb, and showing such sensitivity that (a) it has one restriction site recognized by BamHI,
(b) it has one restriction site recognized by EcoRI,
(c) it has 7 restriction sites recognized by SalI, and
(d) it is not cleaved by BglII, HindIII, KpnI, PstI and XbaI, and a biologically pure culture of a microorganism containing the above plasmid.

3 Claims, 2 Drawing Figures

PLASMID POA15

This invention relates to a novel plasmid, and more specifically, to a circular plasmid derived from Streptomyces and having the property of conferring pock-forming ability on a certain microorganism of the genus Streptomyces.

Plasmids which are extrachromosomal genetic elements are useful as vectors in gene manipulation experiment.

In the field of research work on recombinant DNA, *Escherichia coli* and *Bacillus subtilis* have mainly been used as hosts, and pBR322, pUB110, etc. have been used as vectors.

Microorganisms of the genus Streptomyces are important because of their ability to produce a variety of useful antibiotics and biologically active substances. Gene manipulation of these microorganisms will possibly lead to an increase in the amounts of antibiotics or biologically active substances which they can produce, and to the creation of new useful substances. Much interest has therefore been aroused in this technology. In manipulating genes of Streptomyces, it is considered desirable to utillize hosts and vectors which are derived from Streptomyces. So far, many plasmids isolated from Streptomyces, including pUC 1–10, have been reported (see, for example, Japanese Laid-Open Patent Publications Nos. 133396/1980, 133397/1980, and 120600/1980). These plasmids, however, do not have specified selected markers and are unsuitable as cloning vectors. On the other hand, SCP2 and SLP1-type plasmids confer pock-forming ability on *Streptomyces coelicolor* and *Streptomyces lividans*, respectively, and are actually used for cloning various drug-resistance genes (M. Bibb et al., Nature, 284, 526–531, 1980; C. J. Thompson et al., Nature, 286, 525–527, 1980; and C. J. Thompson et al., J. Bacteriol., 151, 669–677, 1982). Hosts for these plasmids, however, are limited to *Streptomyces coelicolor* and *Streptomyces lividans*, and they cannot be replicated in other various important antibiotic-producing microorganisms. Accordingly, these plasmids have only limited applications as vectors.

In an attempt to isolate a plasmid derivable from Streptomyces which has the character of a selected marker, i.e. the property of imparting pock-forming ability to a certain kind of Streptomyces, and is stable in a host and of which copy number is moderately large, the present inventors selected *Streptomyces griseus* (ATCC 10137) as a host microorganism, and screened, by transformation, plasmids of Streptomyces microorganisms isolated from soils in various districts so as to detect a plasmid capable of conferring pock-forming ability on *Streptomyces griseus*. This work has now led to the discovery of a novel plasmid which has about 20 copies per chromosome, is stable in *Streptomyces griseus* as shown by its low plasmid loss frequency of about 0.6% per life cycle, has a moderate size, and contains restriction sites which are recognized by restriction enzymes BamHI and EcoRI, etc. and considered useful for cloning.

Thus, according to this invention, there is provided a plasmid pOA15 having the property of conferring pock-forming ability on *Streptomyces griseus* (ATCC 10137) and a molecular length of about 10 kb, and showing such sensitivity that (a) it has one restriction site recognized by BamHI,
(b) it has one restriction site recognized by EcoRI,
(c) it has 7 restriction sites recognized by SalI, and
(d) it is not cleaved by BglII, HindIII, KpnI, PstI and XbaI.

The plasmid pOA15 of this invention has the property of conferring pock-forming ability to *Streptomyces griseus* (ATCC 10137).

The term "pock", as used herein, denotes a circular zone of sporulation-inhibition emerged around a strain carrying a certain plasmid when it is inoculated on a lawn of the plasmid-free strain.

The plasmid pOA15 of the present invention has a molecular weight, measured by agarose gel electrophoresis, of about 10.4 kb. This molecular length agrees nearly with its molecular length measured by observation with an electron microscope (Hitachi HS-7D) in accordance with the formamide method of R. W. Davis et al. (see Methods in Enzymology, Vol. 21, 413–428) using pBR 322 (4362 bp) as a standard.

The molecular length, as used in the present application, is measurd by the agarose gel electrophoretic method.

The plasmid pOA15 of this invention has sensitivities to various restriction enzymes as shown in (a) to (d) above. The cleaved fragments obtained by these restriction enzymes have the following molecular length (kb).

(a) BamHI: 10
(b) EcoRI: 10
(c) SalI: 2.9, 2.2, 2.0, 1.8, 0.8, 0.2, 0.1

Furthermore, the plasmid pOA15 of this invention exhibits the following sensitivities to the following restriction enzymes.

(e) It has three restriction sites recognized by BclI I, and its fragments cleaved by BclI have a molecular length (kb) of 4.2, 3.4, 2.4.

(f) It has four restriction sites recognized by BstEII, and its fragments cleaved by BstEII have a molecualr length (kb) of 3.4, 2.6, 2.1, 1.9.

(g) It has six restriction sites recognized by MluI, and its fragments cleaved by MluI have a molecular length (kb) of 3.2, 2.4, 1.8, 1.7, 0.8, 0.1.

(h) It has two restriction sites recognized by PvuII, and its fragments cleaved by PvuII have a molecular length (kb) of 6.1, 3.9.

(i) It is not cleaved by DraI, HpaI, SacI, ScaI, SmaI and XhoI.

The restriction enzyme maps of the plasmid of this invention determined by double digestion are shown in FIG. 1 attached to this application. It is seen from FIG. 1 that the BamHI or EcoRl site of the plasmid pOA15 of this invention is considered to be particularly suitable for cloning foreign DNA.

The plasmid pOA15 of this invention having the characteristics described above is isolated and purified from a microorganism strain of the genus Streptomyces which was isolated from certain soil in Suita City, Osaka-fu, Japan and named Streptomyces sp. OA15 by the present inventors.

The bacteriological properties of this strain are described below.

(a) Morphology

Mycelia show simple branches without verticils. Spore chains consist of a few spores and incomplete spirals, loops, or hooks. Long linear spore chains rarely occur. Several spores often congregate. The surface of the spores is smooth. Neither flagella nor sporangia are observed.

(b) State of growth on the following media (unless specifically indicated, the cultivation was carried out at 28° C.):-

| Medium | Growth | Color of substrate mycelium | Color of aerial mycelium | Soluble pigment |
|---|---|---|---|---|
| Sucrose-nitrate agar | Moderate | Colorless to pale yellow (1ba-2bd) | Hardly any aerial mycelium. Or slightly thick white aerial mycelia formed. | None |
| Glucose-asparagine agar | Good | Pale yellow (2db) to bright yellow (2fb) | White (a) to grayish white | None |
| Glycerin-asparagine agar | Good | Pale yellow (2db) to bright yellow (2fb) | Aerial mycelia partly formed with white spots. | None |
| Starch-inorganic salt agar | Moderate | Pale yellow (2db) to yellowish brown | Slightly white aerial mycelia formed thinly. Later, partly became grayish red brown (5fe) | None |
| Tyrosine agar | Slightly good | Bright brown (4ie), later grayish yellow brown (4ig) | Hardly formed. Sometimes, slightly white aerial mycelia formed partly. | Melanoid pigment formed |
| Nutrient agar | Moderate | Bright brown (4ie) to yellowish brown | White (a) to grayish white | None or a brown pigment slightly formed. |
| Yeast-malt agar | Good | Bright brown to yellowish brown | White to yellowish gray (2dc) | None |
| Oatmeal agar | Good | Pale yellow, later yellowish brown to brown | White, later partly becoming bright grayish red brown | None, or sometimes a reddish brown pigment formed |

(c) Biological properties
(1) Growth temperature: 20° to 37° C., no growth at 45° C.
(2) Liquefaction of gelatin: positive (cultivated at 20° C.)
(3) Hydrolysis of starch: positive
(4) Coagulation of skim milk: negative Peptonization: negative
(5) Formation of melanoid pigment: positive (in any of peptone-yeast extract iron agar, tyrosine agar, and trypton yeast extract broth).

(d) Utilization of the following carbon sources (on the Pridham-Godlieb agar medium)
L-arabinose, D-xylose, D-glucose, D-fructose, sucrose, inositol, L-rhamnose, raffinose and D-mannitol.

A pure culture of the above strain was deposited on Jan. 27, 1983 at Fermentation Research Institute, Agency of Industrial Science and Technology, MITI, at 1-1-3, Higashi, Yatabe-cho, Tsukuba-gun, Ibaraki-ken, Japan under deposit number FERM P 6889 (transferred to international deposition under the Budapest Treaty and accorded international deposit number FERM BP-461 on Jan. 23, 1984).

Isolation and purification of the plasmid from the present strain can be carried out by known methods, for example by the alkali extraction method (Rapid Alkaline Extraction Method; H. C. Birnboim and J. Doly, Nucleic Acids Res., 7, 1513–1523, 1979). More specifically, the plasmid pOA15 can be isolated in a pure form by cultivating the above strain in a nutrient medium containing sucrose and glycine, subjecting the cultivation broth to lysis by treating it with lysozyme and adding a surface-active agent such as sodium dodecylsulfate (SDS), adjusting the lysis mixture to pH 12 with an alkali thereby to denature the chromosomes specifically, removing the denatured chromosomes by centrifugal separation, and subjecting the supernatant liquid to precipitation with ethanol and to cesium chloride (CsCl)-ethidium bromide (EtBr) density gradient ultracentrifugation.

As shown in Referential Example 1 below, the plasmid pOA15 provided by this invention has the property of conferring pock-forming ability on Streptomyces griseus (ATCC 10137), and makes it possible to specify transformants definitely in an experiment of transformation. The transformation frequency is as high as about $10^7$ pocks/microgram DNA, and it is very suitable as a cloning vector.

Furthermore, the plasmid pOA15 provided by this invention, as demonstrated in Referential Examples 2 and 3 given below, has excellent stability in the host microorganism, and the number of copies is moderately large. It is therefore considered very useful as a vector.

As stated above, the plasmid pOA15 of this invention has BamHI and EcoRI restriction sites suitable as sites for inserting foreign DNA. By introducing DNA fragments carrying a drug-resistance gene into such a site, a derivative plasmid which is more useful as a vector plasmid can be formed.

For example, when the BamHI site of the plasmid pOA15 is utilized

wherein A represents adenine, C, cytosine, G, guanine, and T, thymine, and the arrows show cleavage sites), the derivative plasmid can be obtained in the following manner. Chromosomes of Streptomyces rimosus (ATCC 10970) producing tetracycline were cleaved with a restriction enzyme, Sau 3AI

the symbols are the same as above) partially to form DNA fragments having a molecular weight of 2 to 25 kb. The resulting DNA fragments are ligated with DNA fragments of pOA15 cleaved by BamHI to obtain a derivative of the plasmid pOA15 having the DNA fragments of the chromosome of S. rimosus introduced thereinto. In accordance with the method of Thompson et al. (C. J. Thompson et al., J. Bacteriol., 151, 668–677, 1982), protoplasts of Streptomyces griseus (ATCC 10137) are transformed with the resulting plasmid derivative, and after regeneration and sporulation, replicated in an ISP5 medium containing 25 micrograms/ml of tetracycline using a velvet cloth to obtain a tetracycline-resistant strain. By isolating the plasmid from it by the aforesaid rapid alkaline extraction method, there can be obtained a derivative plasmid having tetracycline-resistance genes derived from *S. rimosus* inserted into the BamHI site of the plasmid pOA15. *S. griseus* is retransformed with the resulting hybrid plasmid, and the correlation of the pock-forming ability and the tetracycline resistance is examined. All of the transformants capable of forming pocks showed tetracycline-resistance. Table 1 below summarizes the number of cleavage sites of the resulting typical hybrid plasmids having a molecular length, determined by agarose gel electrophoresis, of about 12.5 kb (pOA151), 14.3 kb (pOA152), 14.6 kb (pOA153), 13.7 kb (pOA154), 13.8 kb (pOA155) and 13.7 kb (pOA156) with regard to various restriction enzymes together with that of the plasmid pOA15 of this invention used as a vector plasmid in cloning.

least two tetracycline-resistance genes which have been separately cloned.

Figure 2:
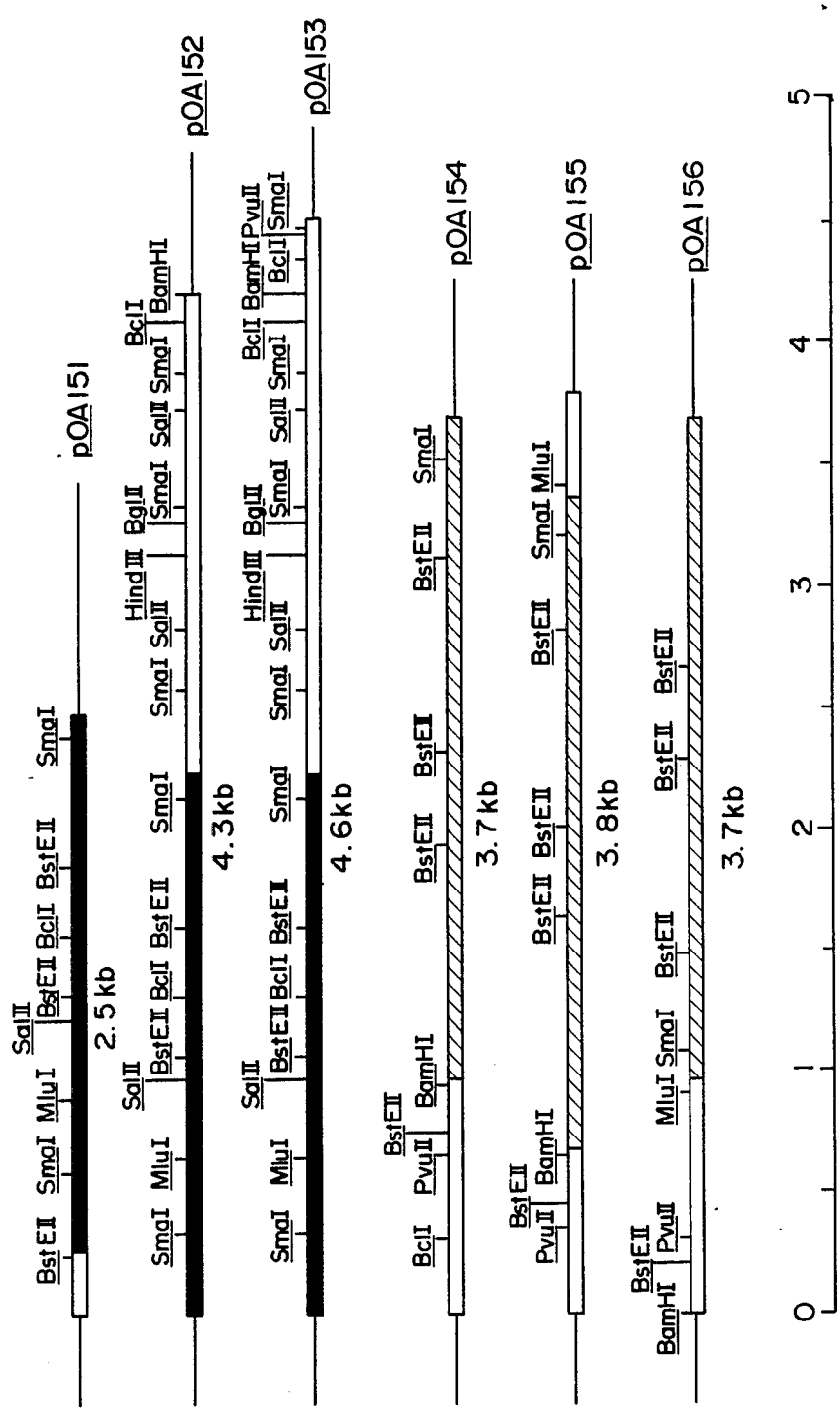

It is clearly seen from FIGS. 1 and 2 that foreign DNA fragments can be introduced into the BamHI, BglII and HindIII sites of pOA152 and pOA153 and the BamHI sites of pOA154, pOA155 and pOA156 without adversely affecting the replication of the plasmids and the property of the plasmids to confer pock-forming ability and tetracycline resistance on the host microorganism. It is also seen from these drawings that foreign DNA fragments can be introduced into the sole EcoRI sites of pOA151, pOA152, pOA153, pOA154, pOA155 and pOA156. Moreover, as shown in Referential Example 4 given hereinafter, these plasmids can transform *Streptomyces griseus* (ATCC 10137) at a frequency of as high as about $5 \times 10^6$/microgram DNA. Furthermore, as shown in Referential Example 5 given below, the

TABLE 1

| Restriction enzyme | Number of cleavage sites by various restriction enzymes |||||||
|---|---|---|---|---|---|---|---|
| | Plasmid |||||||
| | pOA15 | pOA151 | pOA152 | pOA153 | pOA154 | pOA155 | pOA156 |
| BaMHI | 1 | 0 | 1 | 1 | 1 | 1 | 1 |
| Bcl I | 3 | 4 | 5 | 6 | 4 | 3 | 3 |
| Bgl II | 0 | 0 | 1 | 1 | 0 | 0 | 0 |
| Bst EII | 4 | 7 | 6 | 6 | 8 | 8 | 8 |
| Dra I | 0 | 0 | 0 | 0 | 0 | 0 | 0 |
| Eco RI | 1 | 1 | 1 | 1 | 1 | 1 | 1 |
| Hind III | 0 | 0 | 1 | 1 | 0 | 0 | 0 |
| Hpa I | 0 | 0 | 0 | 0 | 0 | 0 | 0 |
| Kpn I | 0 | 0 | 0 | 0 | 0 | 0 | 0 |
| Mlu I | 6 | 7 | 7 | 7 | 6 | 7 | 7 |
| Pst I | 0 | 0 | 0 | 0 | 0 | 0 | 0 |
| Pvu II | 2 | 2 | 2 | 3 | 3 | 3 | 3 |
| Sac I | 0 | 0 | 0 | 0 | 0 | 0 | 0 |
| Sal I | 7 | 8 | 10 | 10 | 7 | 7 | 7 |
| Sca I | 0 | 0 | 0 | 0 | 0 | 0 | 0 |
| Sma I | 0 | 2 | 5 | 6 | 1 | 1 | 1 |
| Xba I | 0 | 0 | 0 | 0 | 0 | 0 | 0 |
| Xho I | 0 | 0 | 0 | 0 | 0 | 0 | 0 |

These hybrid plasmids are each double-digested, in combination with a suitable restriction enzymes, and subjected to agarose electrophoresis. Thus, restriction enzyme cleavage maps of these plasmids are constructed. It has been found that DNA fragments carrying a tetracycline-resistance gene of *Streptomyces rimosus* which have a size of 2.5 kb to 4.6 kb have been introduced into the BamHI site of the plasmid pOA15 characterized by the restriction enzyme cleavage maps of the plasmid pOA15 in FIG. 1 attached to this application. FIG. 2 shows the restriction endonuclease cleavage maps of the inserted DNA fragments (shown by boxes) encoding tetracycline-resistance genes. The left ends of all of these DNA fragments are 1.6 kb apart from EcoRI site of original vector plasmid pOA15 (shown by this line). It is considered from FIG. 2 that a common portion (blackened portion in FIG. 2 of about 2.0 kg exists in pOA151, pOA152 and pOA153, and tetracycline-resistance genes exist at this portion. On the other hand, a common portion (the hatched portion in FIG. 2) of about 2.7 kb exists in pOA154, pOA155 and pOA156, and a tetracycline-resistance gene exists on this fragment. However, no common portion exists in these specific DNA fragments of 2.0 kb and 2.7 kb. It is considered from this that *Streptomyces rimosus* has at plasmid loss frequency per life cycle is less than 1%, and thus the plasmids can be replicated and maintained very stably in the *Streptomyces griseus*.

Of the above derivative plasmids, pOA152 and pOA154 can be isolated by the aforesaid known method from strains which are transformants of *Streptomyces griseus* (ATCC 10137) with these derivative plasmids (which were deposited on Oct. 14, 1983 at Fermentation Research Institute, Agency of Industrial Science and Technology, MITI, Japan and then transferred to international deposition under the Butapest Treaty on Jan. 23, 1984 and accorded deposit numbers FERM BP-462 and FERM BP-463.

As stated hereinabove, the plasmid pOA15 provided by this invention is useful as a vector plasmid for Streptomyces microorganisms.

The following Examples and Referential Examples illustrate the present invention more specifically.

EXAMPLE

Preparation of a plasmid from Streptomyces sp. OA15 (FERM BP-461)

Spores of the OA15 strain were inoculated in a YEME medium (0.3% yeast extract, 0.5% Bacto peptone, 0.3% malt extract and 1.0% glucose) containing 34% sucrose and 0.2% $MgCl_20.6H_2O$, and cultivated at 28° C. for 72 hours in a rotary shaker. The preculture (15 ml) was inoculated in 300 ml of a YEME medium containing 34% sucrose, 0.2% $MgCl_20.6H_2O$ and 0.4% glycine, and cultivated at 28° C. for 24 hours. The culture broth was centrifuged to collect the mycelia. After washing with 12% sucrose, the mycelia were suspended in 32 ml of a solution I (5 mg/ml lysozyme, 50 mM glucose, 10 mM ethylenediaminetetraacetic acid (EDTA) and 25 mM Tris buffer, pH 8.0). Thereafter, 64 ml of a solution II (0.2 N NaOH, 1% SDS) was added, and the mixture was left to stand at 0° C. for 5 minutes. Then, 48 ml of a solution III (3M sodium acetate, pH 4.8) was added, and the mixture was left to stand for 60 minutes. It was then centrifuged, and to the supernatant liquid was added 2.5 times its volume of cold ethanol. The mixture was left to stand at $-20°$ C. for 30 minutes. The mixture was centrifuged, and the precipitate was dissolved in 10 ml of a solution IV (0.1M sodium acetate, 0.05M tris buffer, pH 6.0). The solution was further subjected to ethanol precipitation twice. Finally, the precipitate was dissolved in 5.6 ml of TES buffer (20 mM Tris buffer, pH 8.0, 10 mM EDTA, 50 mM NaCl). To the resulting DNA solution were added 0.3 ml of 10 mg/ml EtBr and 6.0 g of CsCl, and the mixture was subjected to ultracentrifugation at 38,000 rpm at 18° C. for 40 hours by RP 65 T rotor (made by Hitachi Limited). After ultracentrifugation, the plasmid observed by UV lamp irradiation was withdrawn by an injection syringe, and after removing EtBr with butanol, fully dialyzed against TE buffer (10 mM Tris buffer, pH 7.5, 1 mM EDTA). As a result, substantially pure plasmid DNA pOA15 was obtained.

REFERENTIAL EXAMPLE 1

Transformation of *Streptomyces griseus* (ATCC 10137) with pOA15

In the same way as in the preparation of the plasmid, *Streptomyces griseus (ATCC* 10137) was cultivated at 28° C. for 24 hours in 20 ml of a YEME medium containing 34% sucrose, 0.1 $MgCl_2.6H_2O$ and 0.8% glycine. The mycelia were washed twice with 12% sucrose, and suspended in 10 ml of a P3 solution (70 mM NaCl, 5 mM $MgCl_2.6H_2O$, 5 mM $CaCl_2.2H_2O$, 0.5 M sucrose, 25 mM TES [N-tris(hydroxymethyl)methyl-2-aminoethanesulfonic acid], pH 7.2) containing lysozyme (1 mg/ml). The suspension was slowly shaken at 28° C. for 30 minutes to form protoplasts. The protoplasts were separated by centrifugation at 1000×g, and washed twice with 10 ml of a PWP solution (70 mM NaCl, 10 mM $MgCl_2.6H_2O$, 20 mM $CaCl_2.2H_2O$, 0.5M sucrose, 25 mM TES, pH 7.2). The protoplasts were counted by a hemacytometer. It was found that there was obtained a suspension containing about $10^9$/ml of protoplasts. The suspension containing $10^9$/ml of protoplasts was centrifuged, and the supernatant was discarded. The protoplasts were suspended in the small amount of the remaining PWP solution, and 20 microliters of pOA15 DNA solution (about 1 microgram) was added. Immediately then, 0.5 ml of a polyethylene glycol (PEG) solution (2.5% sucrose, 0.1M $CaCl_2.2H_2O$, 1 mM $K_2SO_4$, 50 mM Tris-maleic acid buffer, pH 8.0, 0.2% vol/vol trace element solution [Okanishi et al., J. Gen. Microbiol., 80, 389–400, 1974]) was added, and the mixture was left to stand at room temperature for 1 minute. Then, 5 ml of the PWP solution was added to stop the incorporation of DNA. The mixture was centrifuged, and washed with the PWP solution, and plated on a regeneration medium having the composition to be described below by using a platinum loop. When the proportion of the transformant was large, the mixture was suitably diluted, and after adding protoplasts not carrying pOA15, the mixture was plated on the regeneration medium. After cultivation at 28° C. for 7 days, pocks were observed on the regeneration plate. All pocks contained pOA15. The frequency of transformation was $9.4 \times 10$/microgram DNA when pOA15 prepared from Streptomyces sp. OA15 was used, but rose to $2.4 \times 10^7$/microgram DNA when pOA15 prepared newly from *Streptomyces griseus* (ATCC 10137) was used. This is presumably because *Streptomyces griseus* (ATCC 10137) has unidentified restriction-modification on system.

| Composition of the rengeration medium | |
|---|---|
| Sucrose | 137 g |
| Glucose | 10 g |
| Polypeptone (Daigo) | 4.0 g |
| Yeast extract | 4.0 g |
| $MgCl_2.6H_2O$ | 4.1 g |
| KCl | 0.5 g |
| $K_2HPO_4$ | 0.2 g |
| $CaCl_2.2H_2O$ | 7.4 g |
| TES buffer | 5.7 g |
| Deionized water | 1 liter |
| pH 7.2 | |
| Agar | 22 g |

Referential Example 2

Stability of pOA15 in *Streptomyces griseus* (ATCC 10137)

After transformation of *Streptomyces griseus* (ATCC 10137) with pOA15, the pocks which appeared were transferred to the regeneration medium for sporulation. A spore suspension was prepared therefrom, and after diluting it suitably, plated on the regeneration medium to form colonies. The colonies were replicated on the regeneration plate on which spores of *Streptomyces griseus* (ATCC 10137) not carryng pOA15 were spread thickly so that they grew all over the plate. The pock-forming ability of each colony was evaluated by determining whether a narrow sporulation inhibiting zone was formed around the colony. The proportion of spores which failed to show pock-forming ability after one life cycle was 0.6% (1/158). This is considered to be the percentage of the plasmid loss of pOA15. It was made clear therefore that pOA15 is stable in *Streptomyces griseus* (ATCC 10137).

REFERENTIAL EXAMPLE 3

Copy number of pOA15 in *Streptomyces griseus* (ATCC 10137)

The copy number was determined by a partly modified version of the method of Kieser et al. (T. Kieser et al., Mol. Gen. Genet., 185, 223–238, 1982). Specifically, protoplasts were prepared from *Streptomyces griseus* (ATCC 10137) in the same way as in Referential Example 1. One part by volume of 1% sarkosyl and 25 mM EDTA solution were added to the protoplasts to induce complete lysis. The lysis mixture was kept at 70° C. for 10 minutes to liberate the membrane-bound DNA from the cell residue. After cooling, 1 volume of phenol-chloroform (1:1) solution was added, and the mixture was vigorously stirred. The mixture was then centrifuged to separate it into an aqueous layer and an organic layer. This operation resulted in the removal of proteins. The aqueous layer was precipitated with ethanol, and diluted suitably. Various diluted samples so prepared were subjected to agarose gel electrophoresis. After electrophoresis, the gel was dyed with an EtBr solution (1.0 microgram/ml), and ultraviolet light of short wavelengths was irradiated to introduce cuts into cccDNA. Furthermore, the gel was dyed with the EtBr solution for 1 hour. The gel was photographed by using a Polaroid film 665. The densities of the chromosomes and the plasmid portion in the negative film were quantitatively determined by using a densitometer (Model CS-910, a product of Shimazu Seisakusho Co., Ltd.). Let the size of the chromosomes of Streptomyces griseus (ATCC 10137) be $10^4$ kb (R. Benigni et al., Appl. Microbiol., 30, 180–182, 1977), the number of copies of pOA15 was calculated as about 20 per chromosome from the ratio between the chromosomes and the plasmid obtained above.

REFERENTIAL EXAMPLE 4

Cloning of tetracycline-resistance genes from Streptomyces rimosus (ATCC 10970)

Total DNA of Streptomyces rimosus (ATCC 10970) was obtained by cultivating this strain in a YEME medium (0.3% yeast extract, 0.5% Bacto peptone, 0.3% malt extract, 1.0% glucose) containing 34% sucrose, 0.2% $MgCl_2.6H_2O$ and 0.4% glycine, and then subjecting the culture broth to a lysozyme treatment, a pronase treatment and phenol extraction.

About 9.7 micrograms of DNA obtained by partially digesting the chromosomal DNA of Streptomyces rimosus (ATCC 10970) with a restriction enzyme Sau3AI whose recognition site was ↓GATC, so as to provide DNA fragments having a size of 2 to 25 kb was mixed with 1.5 micrograms of a pock-forming plasmid pOA15 cleaved with BamHI whose recognition site was G↑GATCC, and then they were ligated by using DNA ligase. By using the resulting DNA solution, about $2 \times 10^9$ of protoplasts of Streptomyces griseus (ATCC 10137) were transformed by the method shown in Referential Example 6 given hereinbelow. After regeneration and sporulation of the protoplasts, about $10^6$ pocks were replicated on an ISP5 medium containing 25 micrograms/ml of tetracycline by using a velvet cloth. By cultivation at 28° C. for 3 days, six tetracycline-resistant strains were obtained.

Streptomyces griseus (ATCC 10137) was retransformed by using plasmids prepared from tetracycline-resistance clones in accordance with the method shown in Referential Example 5. After regeneration, the pocks were inoculated in an ISP 5 medium containing tetracycline in a concentration of 25 micrograms/ml. Nearly 100% pocks could grow when six plasmids named pOA151, pOA152, pOA153, pOA154, pOA155 and pOA156 were used. The results of this retransformation experiment suggest that the tetracycline-resistance genes of the Streptomyces rimosus were cloned in the six plasmids.

Referential Example 5

Preparation of pOA151, pOA152, pOA153, pOA154, pOA155 and pOA156

Spores of Streptomyces griseus (ATCC 10137) carrying each of these plasmids were inoculated in a YEME medium containing 34% sucrose, 0.2% $MgCl_2.6H_2O$ and 20 micrograms/ml of tetracycline, and cultivated at 28° C. for 72 hours using a rotary shaker. Fifteen milliliters of the pre-culture was inoculated in 300 ml of a YEME medium containing 34% sucrose, 0.2% $MgCl_2.6H_2O$, 0.8% glycine and 20 micrograms/ml of tetracycline, and cultivated at 28° C. for 24 hours. The culture broth was centrifuged, and the mycelia were collected. The mycelia were washed with 12% sucrose, suspended in 32 ml of a solution I (5 mg/ml lysozyme, 50 mM glucose, 10 mM EDTA, 25 mM Tris buffer, pH 8.0) and the suspension was left at 0° C. for 60 minutes. Thereafter, 64 ml of a solution II (0.2N NaOH, 1% SDS) was added. and the mixture was left to stand at 0° C. for 5 minutes, and then 48 ml of a solution (III) (3M sodium acetate, pH 4.8) was added. The mixture was left to stand at 0° C. for 60 minutes. The mixture was centrifuged, and to the supernatant liquid was added 2.5 times its volume of cold ethanol. The mixture was left to stand at −20° C. for 30 minutes. After centrifugation, the precipitate was dissolved in 10 ml of a solution IV (0.1M sodium acetate, 0.05M tris buffer, pH 8.0). The solution was further precipitated twice with ethanol, and the precipitate was finally dissolved in 5.6 ml of a TES buffer (120 mM tris buffer, pH 8.0, 10 mM EDTA, 50 mM NaCl). To the DNA solution were added 0.3 ml of ethidium bromide (10 mg/ml) and 6.0 g of CsCl were added, and the mixture was subjected to ultra centrifugation at 38,000 rpm and 18° C. for 40 hours. Thereafter, the plasmids observed by UV lamp irradiation were withdrawn from the centrifugal tube by an injection syringe, and after removing ethidium bromide with butanol, fully dialyzed against a TE buffer (10 mM Tris buffer, pH 8.0, 1 mM EDTA). Thus, about 200 micrograms of substantially pure plasmid pOA151, pOA152, pOA153, pOA154, pOA155 or pOA156 was obtained.

REFERENTIAL EXAMPLE 6

Transformation of Streptomyces griseus (ATCC 10137) by a tetracycline-resistant and pock-forming plasmid Streptomyces griseus (ATCC 10137) was cultivated at 28° C. for 24 hours in 20 ml of a YEME medium containing 34% sucrose, 0.1% $MgCl_2.6H_2O$, and 0.8% glycine. The cells were washed twice with 12% sucrose, and suspended in 10 ml of a P3 solution (70 mM NaCl, 5 mM $MgCl_2.6H_2O$, 5 mM $CaCl_2.2H_2O$, 0.5M sucrose, 25 mM TES, pH 7.2) containing 1 mg/ml lysozyme, and the suspension was slowly shaken at 28° C. for 30 minutes to form protoplasts. The suspension was centrifuged at 1000×g for 7 minutes, and the protoplasts were washed twice with 10 ml of a PWP solution (70 mM NaCl, 10 mM $MgCl_2.6H_2O$, 20 mM $CaCl_2.2H_2O$, 0.5M sucrose, 25 mM TES, pH 7.2). A suspension of about $10^9$/ml (by hemacytometer count) of protoplasts were obtained. The suspension was then centrifuged, and the supernatant was discarded. The protoplasts were suspended in the small amount of the remaining PWP solution, and a DNA solution (about 1 microgram) of 20 microliters of pOA151, pOA152, pOA153, pOA154, pOA155 or pOA156 was added. Immediately then, 0.5 ml of a polyethylene glycol (PEG) solution (25% sucrose, 0.1M $CaCl_2.2H_2O$, 1 mM $K_2SO_4$, 50 mM Tris-maleic acid solution, pH 8.0, 0.2% vol/vol trace element solution [M. Okanishi et al., J. Gen. Microbiol., 80, 389–400, 1974]) was added, and the mixture was left to stand at room temperature for 1 minute. Then, 5 ml of the PWP solution was added to stop the incorporation of DNA. The mixture was centrifuged, washed with the PWP solution, and plated on a regeneration medium having the same composition as in Referential Example 1. When it was cultivated at about 28° C. for 7 days, pocks were observed on the regeneration plate. All of the pocks carried a plasmid. The frequency of transformation was about $5 \times 10^6$ pocks/microgram DNA when any of the plasmids pOA151, pOA152, pOA153, pOA154, pOA155 and pOA156 was used. All of the pocks could be grown in the ISP 5 medium containing 25 micrograms/ml of tetracycline, and were resistant to tetracycline.

REFERENTIAL EXAMPLE 7

Stability of the tetracycline-resistant and pock-forming plasmids in *Streptomyces griseus* (ATCC 10137)

*Streptomyces griseus* (ATCC 10137) was transformed with pOA151, pOA152, pOA153, pOA154, pOA155 or pOA156. The pocks which appeared after transformation were transferred to the regeneration medium to form spores. A spore suspension was prepared therefrom, and suitably diluted. The diluted suspension was plated on the regeneration medium to form colonies. The colonies were inoculated in an ISP 5 medium containing 25 micrograms/ml of tetracycline by a toothpick, and the ratio of the grown colonies to those examined was determined. The results are tabulated below.

| Plasmid | Stability (% of plasmid-carrying strain after one life cycle) |
|---|---|
| pOA151 | 100 (156/156)* |
| pOA152 | 100 (82/82) |
| pOA153 | 99 (155/156) |
| pOA154 | 99 (155/156) |
| pOA155 | 99 (102/103) |
| pOA156 | 99 (154/156) |

*The parenthesized figures show the number of colonies examined (denominator) and the number of grown colonies (numerator).

The tetracycline-resistant strains are considered to be plasmid strains. Thus, it has been made clear that all the tetracyline-resistance and pock-forming plasmids are very stable in the *Streptomyuces griseus*.

What we claim is:

1. A biologically pure plasmid pOA15 in isolated form having the property of conferring pock-forming ability on *Streptomyces griseus* (ATCC 10137) and a molecular length of about 10 kb, and further having
   (a) one restriction site recognized by BamHI,
   (b) one restriction site recognized by EcoRI,
   (c) 7 restriction sites recognized by SalI, and
   (d) not being cleavable at the BglII, HindIII, KpnI, PstI and XbaI restriction sites.

2. A biologically pure culture of a microorganism containing a plasmid as defined in claim 1, wherein the microorganism is a species of the genus Streptomyces.

3. The biologically pure culture of claim 4 wherein said microorganism is Streptomyces sp. OA15 deposited with FRI under PERM BP-461.

* * * * *